United States Patent [19]
Palermo et al.

[11] Patent Number: 5,749,837
[45] Date of Patent: May 12, 1998

[54] ENHANCED LUBRICITY GUIDEWIRE

[75] Inventors: Thomas J. Palermo, Palo Alto; Gene Samson, Milpitas; Gregory E. Mirigian, Fremont; U. Hiram Chee, San Carlos, all of Calif.

[73] Assignee: Target Therapeutics, Inc., Fremont, Calif.

[21] Appl. No.: 695,185

[22] Filed: Aug. 1, 1996

Related U.S. Application Data

[63] Continuation of Ser. No. 346,143, Nov. 29, 1994, abandoned, which is a continuation-in-part of Ser. No. 62,456, May 11, 1993, Pat. No. 5,409,015.

[51] Int. Cl.$^6$ .................................... A61B 5/00
[52] U.S. Cl. .................................... 600/585
[58] Field of Search .................... 128/657, 658, 128/772; 604/164, 170, 180, 280–282

[56] References Cited

U.S. PATENT DOCUMENTS

| | | |
|---|---|---|
| Re. 33,911 | 5/1992 | Samson et al. . |
| 2,221,138 | 11/1940 | Hendrickson . |
| 2,279,297 | 4/1942 | Bry . |
| 2,905,178 | 9/1959 | Hilzinger, III . |
| 3,174,851 | 3/1965 | Buehler et al. . |
| 3,338,046 | 8/1967 | Baur et al. . |
| 3,351,463 | 11/1967 | Rozner et al. . |
| 3,416,531 | 12/1968 | Edwards . |
| 3,452,742 | 7/1969 | Muller . |
| 3,528,406 | 9/1970 | Jeckel et al. . |
| 3,547,103 | 12/1970 | Cook . |
| 3,552,384 | 1/1971 | Pierie et al. . |
| 3,753,700 | 8/1973 | Harrison et al. . |
| 3,757,768 | 9/1973 | Kline . |
| 3,789,841 | 2/1974 | Antoshkiw . |
| 3,890,977 | 6/1975 | Wilson . |
| 3,941,119 | 3/1976 | Corrales . |
| 3,973,556 | 8/1976 | Fleischhacker et al. . |
| 4,003,369 | 1/1977 | Heilmann et al. . |
| 4,020,829 | 5/1977 | Willson et al. . |
| 4,178,810 | 12/1979 | Takahashi . |
| 4,215,703 | 8/1980 | Willson . |
| 4,430,083 | 2/1984 | Ganz et al. . |
| 4,538,622 | 9/1985 | Samson et al. . |
| 4,545,390 | 10/1985 | Leary . |
| 4,554,929 | 11/1985 | Samson et al. . |
| 4,619,274 | 10/1986 | Morrison . |
| 4,665,906 | 5/1987 | Jervis et al. . |
| 4,721,117 | 1/1988 | Mar et al. . |
| 4,739,768 | 4/1988 | Engelson . |
| 4,770,188 | 9/1988 | Chikama . |

(List continued on next page.)

FOREIGN PATENT DOCUMENTS

| | | |
|---|---|---|
| 0014424 | 8/1980 | European Pat. Off. . |
| 0382974 | 8/1990 | European Pat. Off. . |
| 0491349 | 6/1992 | European Pat. Off. . |
| 0515201 | 11/1992 | European Pat. Off. . |
| 0519604 | 12/1992 | European Pat. Off. . |
| 4-9162 | 1/1992 | Japan . |
| WO 91/15152 | 10/1991 | WIPO . |
| WO 92/14506 | 9/1992 | WIPO . |

OTHER PUBLICATIONS

Kikuchi et al., "A new guidewire with kink-resistant core and low-friction coating" *Cardiovasc. Intervent. Radiol.* (1989) 12:107–109.

*Primary Examiner*—Max Hindenburg
*Attorney, Agent, or Firm*—Morrison & Foerster, LLP

[57] ABSTRACT

This invention is a surgical device. It is a guidewire for use in a catheter and is used for accessing a targeted site in a lumen system of a patient's body. The guidewire or guidewire section may be of a stainless steel or a high elasticity metal alloy, preferably a Ni—Ti alloy, having specified physical parameters. The guidewire is especially useful for accessing peripheral or soft tissue targets. A special variation of the inventive guidewire includes the coating of the wire with a tie layer and then with a one or more lubricious polymers to enhance its suitability for use within catheters and with the interior of vascular lumen.

24 Claims, 5 Drawing Sheets

U.S. PATENT DOCUMENTS

| | | | |
|---|---|---|---|
| 4,790,624 | 12/1988 | Van Hoye et al. | 128/4 |
| 4,846,186 | 7/1989 | Box et al. . | |
| 4,925,445 | 5/1990 | Sakamoto et al. . | |
| 4,934,380 | 6/1990 | de Toledo . | |
| 4,966,163 | 10/1990 | Kraus et al. . | |
| 4,969,890 | 11/1990 | Sugita et al. . | |
| 4,971,490 | 11/1990 | Hawkins . | |
| 4,984,581 | 1/1991 | Stice . | |
| 4,991,602 | 2/1991 | Amplatz et al. . | |
| 4,998,923 | 3/1991 | Samson et al. . | |
| 5,019,040 | 5/1991 | Itaoka et al. | 604/95 |
| 5,042,985 | 8/1991 | Elliott et al. . | |
| 5,050,606 | 9/1991 | Tremulis . | |
| 5,069,226 | 12/1991 | Yamauchi et al. . | |
| 5,095,915 | 3/1992 | Engelson . | |
| 5,111,829 | 5/1992 | Alvarez de Toledo . | |
| 5,120,308 | 6/1992 | Hess . | |
| 5,129,890 | 7/1992 | Bates et al. . | |
| 5,143,085 | 9/1992 | Wilson et al. . | |
| 5,144,959 | 9/1992 | Gambale et al. . | |
| 5,171,383 | 12/1992 | Sagaye et al. . | |
| 5,213,111 | 5/1993 | Cook et al. . | |
| 5,230,348 | 7/1993 | Ishibe et al. . | |
| 5,238,004 | 8/1993 | Sahatjian et al. . | |
| 5,267,574 | 12/1993 | Viera et al. | 128/772 |
| 5,333,620 | 8/1994 | Moutafis et al. | 128/772 |
| 5,341,818 | 8/1994 | Abrams et al. | 128/772 |
| 5,406,960 | 4/1995 | Corso, Jr. | 128/772 |
| 5,443,907 | 8/1995 | Slaikeau et al. | 128/772 |
| 5,498,250 | 3/1996 | Prather . | |

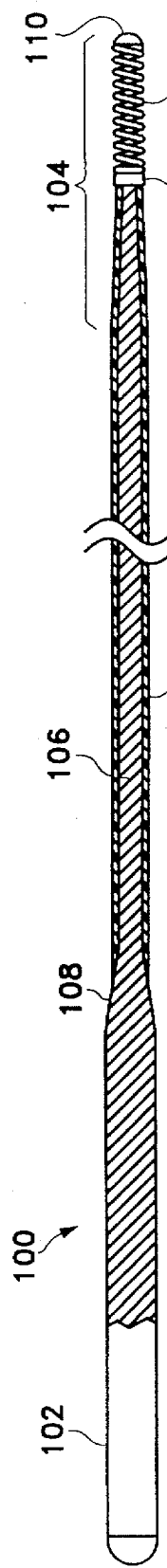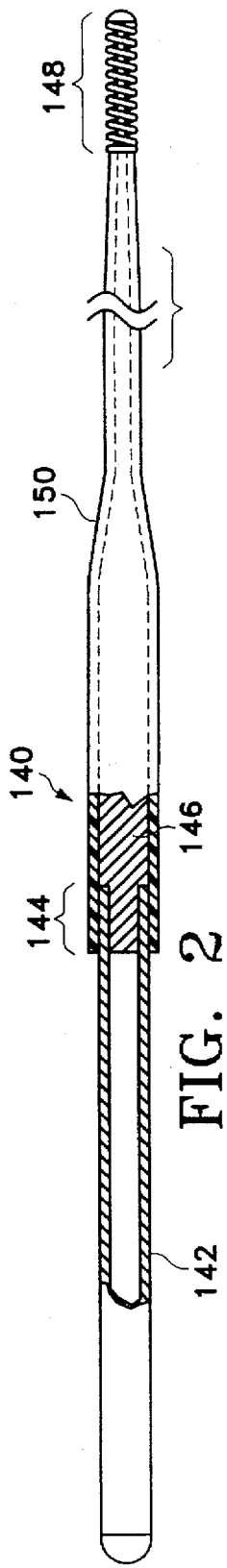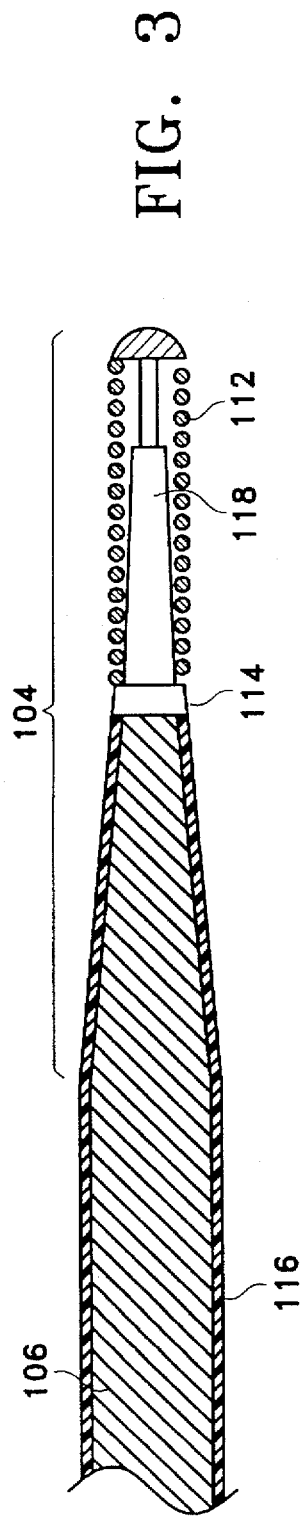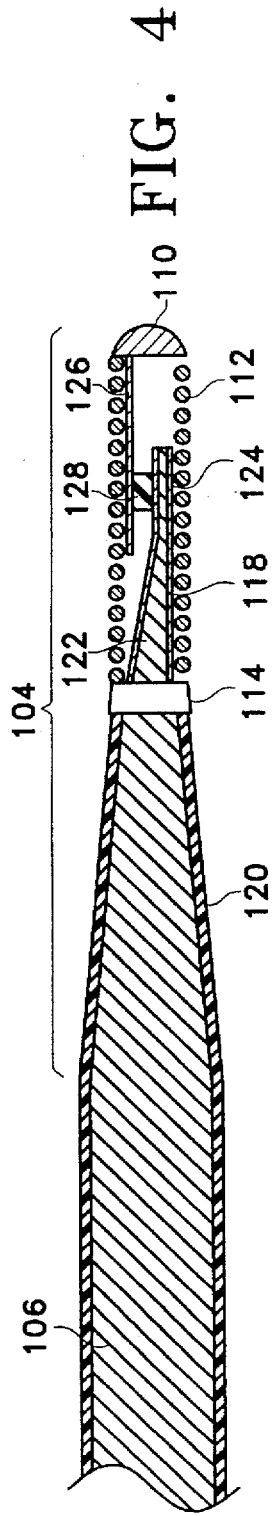

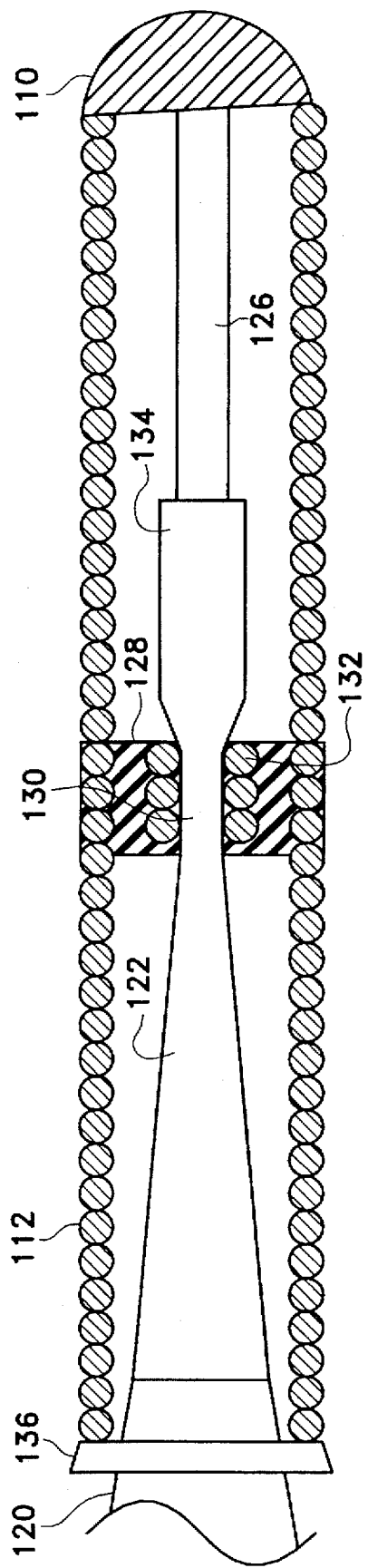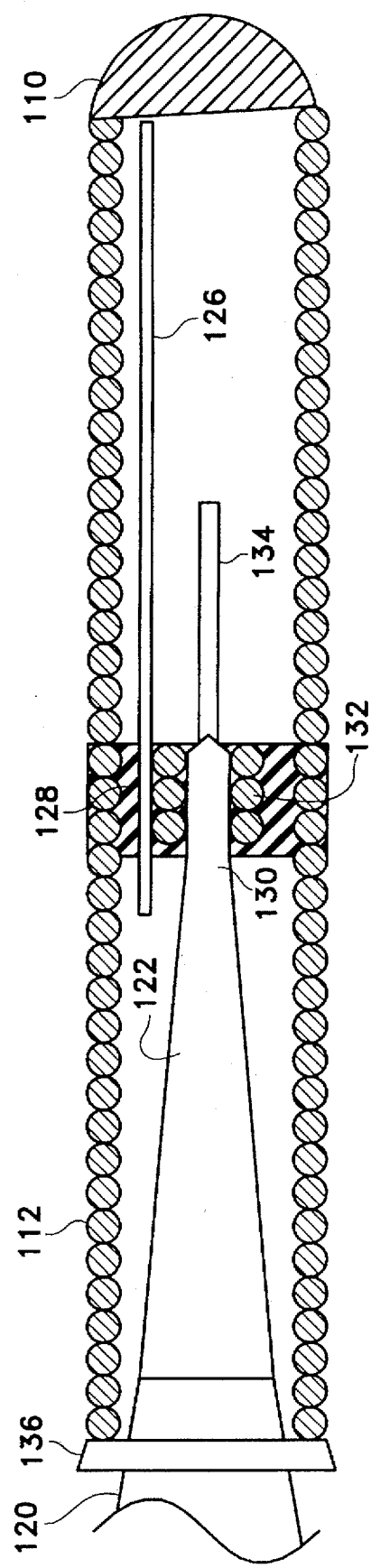

ENHANCED LUBRICITY GUIDEWIRE

The instant application is a continuation of application Ser. No. 08/346,143, filed Nov. 29, 1994, now abandoned, which is a continuation-in part of U.S. Ser. No. 08/062,456, filed May 11, 1993, now U.S. Pat. No. 5,409,015.

FIELD OF THE INVENTION

This invention is a surgical device. It is a guidewire for use in a catheter and is used for accessing a targeted site in a lumen system of a patient's body. The guidewire or guidewire section may be of a stainless steel or a high elasticity metal alloy, preferably a Ni—Ti alloy, having specified physical parameters. The guidewire is especially useful for accessing peripheral or soft tissue targets. A special variation of the inventive guidewire includes the coating of the wire with a tie layer and then with a one or more lubricious polymers to enhance its suitability for use within catheters and with the interior of vascular lumen.

BACKGROUND OF THE INVENTION

Catheters are used increasingly as a means for delivering diagnostic and therapeutic agents to internal sites within the human body that can be accessed through the various of the body's lumen systems, particularly through the vasculature. A catheter guidewire is used for guiding the catheter through the bends, loops, and branches forming the blood vessels within the body. One method of using a guidewire to direct the catheter through the torturous paths of these systems of lumen involves the use of a torqueable guidewire which is directed as a unit from a body access point such as the femoral artery to the tissue region containing the target site. The guidewire is typically bent at its distal end, and may be guided by alternately rotating and advancing the guidewire along the small vessel pathway to the desired target. Typically the guidewire and the catheter are advanced by alternately moving the guidewire along a distance in the vessel pathway, holding the guidewire in place, and then advancing the catheter along the axis of the guidewire until it reaches the portion of the guidewire already advanced farther into the human body.

The difficulty in accessing remote body regions, the body's periphery or the soft tissues within the body such as the brain and the liver, are apparent. The catheter and its attendant guidewire must be both flexible, to allow the combination to follow the complicated path through the tissue, and yet stiff enough to allow the distal end of the catheter to be manipulated by the physician from the external access site. It is common that the catheter is as long as a meter or more.

The catheter guidewires used in guiding a catheter through the human vasculature have a number of variable flexibility constructions. For instance, U.S. Pat. Nos. 3,789,841; 4,545,390; and 4,619,274 show guidewires in which the distal end section of the wire is tapered along its length to allow great flexibility in that remote region of the guidewire. This is so, since the distal region is where the sharpest turns are encountered. The tapered section of the wire is often enclosed in a wire coil, typically a platinum coil, to increase the column strength of the tapered wire section without significant loss of flexibility in that region and also to increase the radial capacity of the guidewire to allow fine manipulation of the guidewire through the vasculature.

Another effective guidewire design is found in U.S. Pat. No. 5,095,915 which shows a guidewire having at least two sections. The distal portion is encased in an elongated polymer sleeve having axially spaced grooves to allow increased bending flexibility of the sleeve.

Others have suggested the use of guidewires made of various super-elastic alloys in an attempt to achieve some of the noted functional desires.

U.S. Pat. No. 4,925,445, to Sakamoto et al., suggests the use of a two-portion guidewire having a body portion relatively high in rigidity and a distal end portion which is comparatively flexible. At least one portion of the body and the distal end portions is formed of super-elastic metallic materials. Although a number of materials are suggested, including Ni—Ti alloys of 49 to 58% (atm) nickel, the patent expresses a strong preference for Ni—Ti alloys in which the transformation between austentite and martensite is complete at a temperature of 10° C. or below. The reason given is that "for the guidewire to be useable in the human body, it must be in the range of 10° to 20° C. due to anesthesia at a low body temperature." The temperature of the human body is typically about 37° C.

Another document disclosing a guidewire using a metal alloy having the same composition as a Ni—Ti super-elastic alloy is WO91/15152 (to Sahatjian et al. and owned by Boston Scientific Corp.). That disclosure suggests a guidewire made of the precursor to the Ni—Ti elastic alloy. Super-elastic alloys of this type are typically made by drawing an ingot of the precursor alloy while simultaneously heating it. In the unstressed state at room temperature, such super-elastic materials occur in the austenite crystalline phase and, upon application of stress, exhibit stress-induced austenite-martensite (SIM) crystalline transformations which produce nonlinear elastic behavior. The guidewires described in that published application, on the other hand, are said not to undergo heating during the drawing process. The wires are cold-drawn and great pain is taken to assure that the alloy is maintained well below 300° F. during each of the stages of its manufacture. This temperature control is maintained during the step of grinding the guidewire to form various of its tapered sections.

U.S. Pat. No. 4,665,906 suggests the use of stress-induced martensite (SIM) alloys as constituents in a variety of different medical devices. Such devices are said to include catheters and cannulas.

U.S. Pat. No. 4,969,890 to Sugita et al., suggests the production of a catheter having a main body fitted with a shape memory alloy member, and having a liquid injection means to supply a warming liquid to allow the shape memory alloy member to recover its original shape upon being warmed by the fluid.

U.S. Pat. No. 4,984,581, to Stice, suggests a guidewire having a core of a shape memory alloy, the guidewire using the two-way memory properties of the alloy to provide both tip-deflecting and rotational movement to the guidewire in response to a controlled thermal stimulus. The controlled thermal stimulus in this instance is provided through application of an RF alternating current. The alloy selected is one that has a transition temperature between 36° C. and 45° C. The temperature 36° C. is chosen because of the temperature of the human body; 45° C. is chosen because operating at higher temperatures could be destructive to body tissue, particularly some body proteins.

U.S. Pat. No. 4,991,602 to Amplatz et al., suggests a flexible guidewire made up of a shape memory alloy such as the nickel-titanium alloy known as nitinol. The guidewire is one having a single diameter throughout its midcourse, is tapered toward each end, and has a bead or ball at each of those ends. The bead or ball is selected to allow ease of movement through the catheter into the vasculature. The guidewire is symmetrical so that a physician cannot make a wrong choice in determining which end of the guidewire to insert into the catheter. The patent suggests that wound wire coils at the guidewire tip are undesirable. The patent further suggests the use of a polymeric coating (PTFE) and an anticoagulant. The patent does not suggest that any particular type of shape memory alloy or particular chemical or physical variations of these alloys are in any manner advantageous.

Another catheter guidewire using Ni—Ti alloys is described in U.S. Pat. No. 5,069,226, to Yamauchi, et al. Yamauchi et al. describes a catheter guidewire using a Ni—Ti alloy which additionally contains some iron, but is typically heat-treated at a temperature of about 400° to 500° C. so as to provide an end section which exhibits pseudo-elasticity at a temperature of about 37° C. and plasticity at a temperature below about 80° C. A variation is that only the end portion is plastic at the temperatures below 80° C.

U.S. Pat. No. 5,171,383, to Sagae, et al., shows a guidewire produced from a super-elastic alloy which is then subjected to a heat treatment such that the flexibility is sequentially increased from its proximal portion to its distal end portions. A thermoplastic coating or coil spring may be placed on the distal portion of the wire material. Generally speaking, the proximal end portion of the guidewire maintains a comparatively high rigidity and the most distal end portion is very flexible. The proximal end section is said in the claims to have a yield stress of approximately five to seven kg/mm$^2$ and an intermediate portion of the guidewire is shown in the claims to have a yield stress of approximately 11 to 1 kg/mm$^2$.

Published European Patent Application 0,515,201-A1 also discloses a guidewire produced at least in part of a superelastic alloy. The publication describes a guidewire in which the most distal portion can be bent or curved into a desired shape by a physician immediately prior to use in a surgical procedure. Proximal of the guide tip, the guidewire is of a superelastic alloy. Although nickel-titanium alloys are said to be most desirable of the class shown in that disclosure, no particular physical description of those alloys is disclosed to be any more desirable than another.

Published European Patent Application 0,519,604-A2 similarly discloses a guidewire which may be produced from a superelastic material such as nitinol. The guidewire core is coated with a plastic jacket, a portion of which may be hydrophilic and a portion of which is not.

Examples of Ni—Ti alloys are disclosed in U.S. Pat. Nos. 3,174,851; 3,351,463; and 3,753,700.

None of these disclosures suggest the guidewire composition or configuration described below.

SUMMARY OF THE INVENTION

This invention is a guidewire, preferably a guidewire suitable for introduction into the vasculature of the brain, and a method for its use. At least a distal portion of the guidewire may be of a super-elastic alloy which preferably is a Ni—Ti alloy having specific physical characteristics, e.g., a stress-strain plateau at about 75+10 ksi and another at 25+7.5 ksi (each measured at 3% strain) when the stress-strain relationship is measured to a strain of 6%.

A highly desirable variation of the inventive guidewire comprises a long wire having a proximal section, an intermediate section, and a distal section. The guidewire further may have an eccentricity ratio of 1±10$^{-4}$. The distal end section is typically the most flexible of the sections and is at least about three centimeters long. Desirably, the flexible distal end section is partially tapered and is covered by a coil assembly which is connected to the distal end of the guidewire at its distal tip. The coil assembly may be attached to the distal tip by soldering, perhaps after plating or coating the distal end section with a malleable or solderable metal, such as gold.

The guidewire whether of a super-elastic metal or not may be coated with a polymer or other material to enhance its ability to traverse the lumen of the catheter. A lubricious polymer may be placed directly upon the core wire or upon a "tie" layer. The tie layer may be a shrink-wrap tubing or a plasma deposition or may be a dip, spray, or fusion spray coating of an appropriate material. The tie layer may also be radio opaque.

The guidewire of this invention may be of a composite in which a distal portion of the core is a super-elastic alloy of the type described below and the more proximal section or sections are of another material or configuration, e.g., stainless steel wire or rod, stainless steel hypotube, super-elastic alloy tubing, carbon fiber tubing, etc.

Ideally there will be one or more radiopaque markers placed upon the guidewire, e.g., at its distal tip and potentially along the length of the intermediate section. These markers may be used both to enhance the guidewire's radiopacity and its ability to transmit torque from the proximal end to the distal end while maintaining a desired flexibility.

This invention also includes a catheter apparatus made up of the guidewire core and a thin-walled catheter designed to be advanced along the guidewire through the vasculature for positioning at a desired site.

BRIEF DESCRIPTION OF THE DRAWINGS

FIG. 1 shows a schematic side view (not to scale) of the major components of the inventive guidewire.

FIG. 2 is a partial cutaway, side view of composite guidewire according to this invention having a distal portion of a highly elastic alloy.

FIG. 3 is a partial cutaway side view of one embodiment of the distal tip of the FIG. 1 device.

FIG. 4 is a partial cutaway side view of a second embodiment of the distal tip of the FIG. 1 device.

FIG. 5A is a partial cutaway side view of a third embodiment of the distal tip of the FIG. 1 device.

FIG. 5B is a partial cutaway top view of the embodiment shown in FIG. 5A.

DESCRIPTION OF THE INVENTION

Figure 6A:
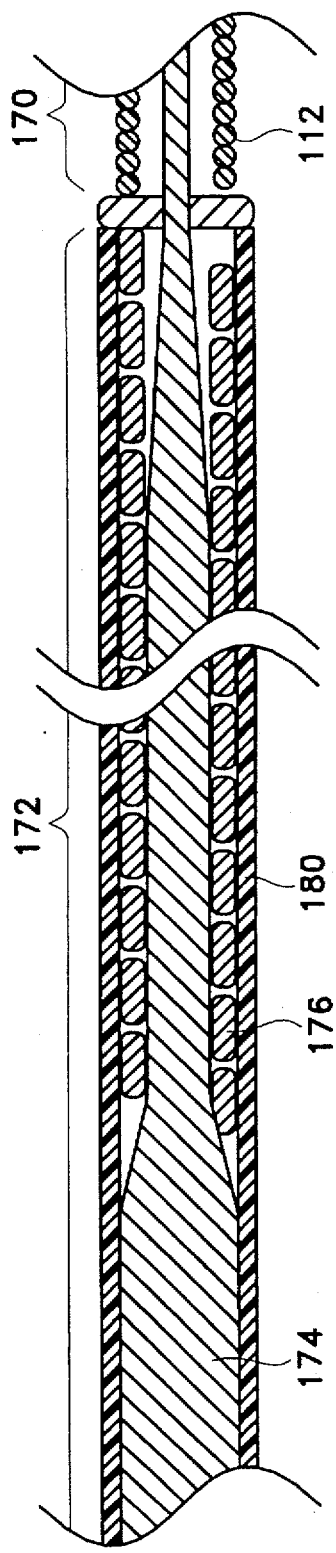
FIGS. 6A and 6B show midsection variations, in fragmentary cross-section, of the invention guidewire.

FIG. 1 shows an enlarged side view of a guidewire made according to a very desirable variation of the inventive guidewire (100). The guidewire (100) is made up of the wire core formed of a flexible torqueable wire filament material, of the alloys described below, and has a total length typically between about 50 and 300 centimeters. The proximal section (102) preferably has a uniform diameter (along its length) of about 0.010 to 0.025 inches, preferably 0.010 to 0.018 inches. The relatively more flexible distal section (104) extends for 3 to 30 centimeters or more of the distal end of the guidewire (100). There may be a middle section (106) having a diameter intermediate between the diameter of the two portions of the wire adjoining the middle section. The middle section (106) may be continuously tapered, may have a number of tapered sections or sections of differing diameters, or may be of a uniform diameter along its length. If middle section (106) is of a generally uniform diameter, the guidewire core will neck down as is seen at (108). The distal section (104) of the guidewire (100) typically has an end cap (110), a fine wire coil (112), and a solder joint (114). The fine wire coil (112) may be radiopaque and made from materials including but not limited to platinum and its alloys. Specific inventive variations of the distal section (104) are described below. The end cap (110) may be radiopaque to allow knowledge of the position of the coil (112) during the process of inserting the catheter and traversal of the guidewire through the vasculature. All or part of the guidewire proximal section (102) and middle section (106) and distal section (104) may be coated with a thin layer (116) of polymeric material to improve its lubricity without adversely affecting the flexibility or shapeability of the guidewire. This invention includes portions or sections of the guidewire described above having the noted polymeric tie layer described below and a slippery, e.g., a hydrophilic polymeric coating thereon.

FIG. 2 shows a variation of the inventive guidewire which is a composite, e.g., a distal portion of the guidewire core is produced of the specified alloy and the composite is of another material or configuration. In particular, the composite guidewire (140) is made up of a proximal section (142) that is a section of small diameter tubing of, e.g., an appropriate stainless steel or high elasticity alloy such as those discussed elsewhere herein. The tubular proximal section (142) is attached by soldering or by gluing or by other joining method suitable for the materials involved at the joint (144) to a distal section (146) that extends to the distal end of the composite guidewire assembly (140). The distal tip (148) of the catheter assembly (140) may be of the same configuration as those otherwise described herein. The catheter assembly may be coated (150) with polymeric material, as desired.

FIG. 3 shows a partial cutaway of one embodiment of the distal section (104) and the distal end of the intermediate section (106). The metallic guidewire core is shown partially coated with polymer (116) and a malleable metal coating (118) on the tapered portion of the distal tip. The malleable metal may be selected from suitable radiopaque materials such as gold or other easily solderable materials such as silver, platinum, palladium, rhodium, and alloys of the above. The tip also includes a radiopaque coil (112) which is bounded on its proximal end by a solder joint (114) and is joined with the end of the guidewire at (110). The radiopaque coil (112) may be made of known suitable materials such as platinum, palladium, rhodium, silver, gold, and their alloys. Preferred is an alloy containing platinum and a small amount of tungsten. The proximal and distal ends of coil (112) may be secured to the core wire by soldering.

FIG. 4 shows a partial cutaway of another embodiment of the distal section (104) of the inventive guidewire. In this embodiment, the metal guidewire core has a proximal tapered portion (120), a distal tapered section (122) with a solder joint (114) separating the two sections, and a constant diameter tip (124). The distal tip (124) may have constant diameter typically between about 0.002 and 0.005 inches, preferably about 0.003 inches. The distal tip (124) is preferably between about 1 and 5 cm in length, preferably about 2 cm but the portion of constant diameter extends for at least about 25% of the distance between the solder joint (128) and the solder joint (114). This constant diameter section marginally stiffens the distal tip assembly for enhanced control. The entire distal section (104) desirably is between about 20 and 50 cm, preferably about 25 cm in length. The maximum diameter of the proximal tapered portion (120) of the guidewire core typically is between about 0.005 and 0.020 inches, preferably about 0.010 inches. The distal tapered portion (122) and distal tip (124) are again shown with a malleable metal coating (118) such that the distal tapered portion (122) and distal tip (124) stay bent upon forming by the physician. In this embodiment, the fine wire coil (112) is bounded on its proximal end by a solder joint (114) and on its distal end by an end cap (110). The end cap (110) is connected to the guidewire by means of a metallic ribbon (126). The ribbon (126) may be made of stainless steel, platinum, palladium, rhodium, silver, gold, tungsten, and their alloys or other materials which are plastic and that are easily soldered. The ribbon (126) is soldered to the fine wire coil (112) and to the distal tip (124) of the distal section (104) of the guidewire at a solder joint (128) such that the end cap (110) is secured against the fine wire coil (112).

FIGS. 5A and 5B show yet another inventive embodiment of the distal section (104) of the guidewire (100). FIG. 5A shows a side view, partial cutaway of the inventive guidewire. The fine wire coil (112) may be bounded by a polymer adhesive (136) that joins the coil (112) to the core wire and an end cap (110) and further secured to the guidewire core by a solder joint (128). In this embodiment, the distal section (104) of the guidewire again comprises a tapered portion (120) that is proximal to the polymer adhesive (136) and a tapered portion (122) that is distal to the polymer adhesive (136). The distal section (104) also comprises a smaller diameter portion (130) or "neck" that may be surrounded by optional inner coil (132). The inner coil (132) may be made of a suitable metallic material preferably that is easy to solder and preferably radiopaque. It is preferably platinum or stainless steel. One way to produce neck (130) is to flatten the distal portion of the guidewire (134) distal to the neck so that the resulting spade (134) is no longer of circular cross-section but rather is of rectangular shape. This may be more easily visualized in FIG. 5B since that Figure shows a cutaway top view of the guidewire shown in FIG. 5A. As in above-described embodiments, the end cap (110) is secured to the guidewire by a metallic ribbon (126). The solder joint (128) secures the guidewire core to the inner helical coil (132) which secures the end cap (110) via the ribbon (126) and further secures the outer fine wire coil (112). This configuration is especially valuable for use with guidewire materials which are not easily solderable. The solder joint need not adhere to the guidewire and yet the inner coil (132), ribbon (126), and outer fine wire coil (112) all are maintained as a single integral unit and have no chance of slipping proximally or distally on the guidewire assembly.

Although the embodiment described with reference to FIGS. 5A and 5B speaks generally of a guidewire made of a high elasticity alloy, materials for the guidewire and the ribbon such as stainless steel, platinum, palladium, rhodium and the like are suitable with that embodiment.

Figure 6B:
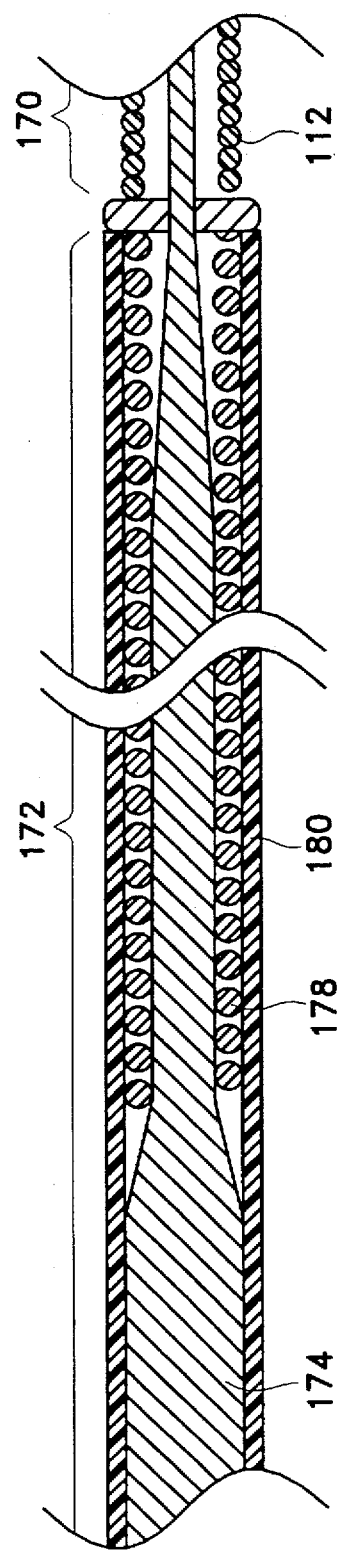

FIGS. 6A and 6B show partial fragmentary cross-sections of portions of the distal section (170) and the midsection (172) of a variation of the inventive catheter assembly. In the variations shown in FIGS. 6A and 6B, the core is ground to a smaller diameter to achieve a higher degree of flexibility in those regions. To provide additional column strength and torqueability, a flat wound ribbon (176) (in FIG. 6A) or coil (178) (in FIG. 6B). In addition, since many of the super-elastic alloys making up core (174) are not particularly radiopaque, it is often desirable to use radiopaque materials for the ribbon (176) or coil (178) so to permit the physician to observe the position of the guidewire assembly with greater ease. Indeed, it is not uncommon for the ribbons (176) or coils (178) to extend (in conjunction with the coils (112)) to extend 25–35 cm. from the distal tip of the catheter assembly. Again, it is not uncommon for the distal coil (112) to be itself up to 10 cm. or so in length. Finally, it is desirable to use a smaller diameter wire in the more proximal coil (178) than the distal coil (112) to provide a radiopaque view and enhanced column strength to the guidewire belt with lower overall mass.

In addition, we have found it desirable to coat all or part of the guidewire core (as will be discussed in more detail below) with a lubricious coating material such as polyfluorocarbons or with hydrophilic polymers. As is discussed below, when using hydrophilic polymers as the coating material, it is often desirable to use a tie layer on the guidewire core. The composition of such tie layers will be also discussed below. However, in the variation shown in FIGS. 6A and 6B, the combination of tie layer and hydrophilic polymer (180) is shown as being placed over the midsection stiffeners (176) and (178).

Figure 7:
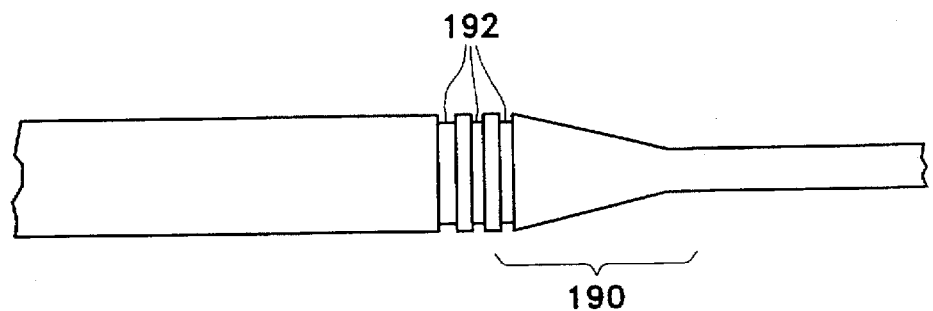
FIG. 7 is a partial side view of a midsection joint in the inventive guidewire.

FIG. 7 is a partial side view of a midsection joint in the inventive guidewire. On many variations of the inventive guidewire, various sections of the core are joined by tapered sections such as seen at (190). This means that the guidewire core is significantly stiffer at the proximal end of the tapered joint (190). We have found that it is sometimes desirable to place grooves (192) in that proximal end to lower the overall stiffness of the guidewire at that junction and yet retain the columnar strength.

GUIDEWIRE CORE

This guidewire is typically used in a catheter which is made up of an elongate tubular member having proximal and distal ends. The catheter is (again) about 50 to 300 centimeters in length, typically between about 100 and 200 centimeters in length. Often, the catheter tubular member has a relatively stiff proximal section which extends along a major portion of the catheter length and one or more relatively flexible distal sections which provide greater ability of the catheter to track the guidewire through sharp bends and turns encountered as the catheter is advanced through the torturous paths found in the vasculature. The construction of a suitable catheter assembly having differential flexibility along its length is described in U.S. Pat. No. 4,739,768.

We have found that certain alloys, particularly Ni—Ti alloys, retain their super-elastic properties during traversal through the vasculature and yet are sufficiently pliable that they provide the physician using the guidewire with enhanced "feel" or feedback and yet do not "whip" during use. That is to say, as a guidewire is turned it stores energy during as a twist and releases it precipitously as it "whips" to quickly recover the stored stress. The preferred alloys do not incur significant unrecovered strain during use. We have also found that if the eccentricity of the wire, i.e., the deviation of the cross-section of the guidewire from "roundness" (particularly in the middle section) is maintained at a very low value, the guidewire is much easier to steer or direct through the vasculature.

The material used in the guidewires of this invention are of shape memory alloys which exhibit super-elastic/pseudo-elastic shape recovery characteristics. These alloys are known. See, for instance, U.S. Pat. Nos. 3,174,851 and 3,351,463 as well as 3,753,700; however, the '700 patent describes a less desirable material because of the higher modulus of the material due to an increased iron content. These metals are characterized by their ability to be transformed from an austenitic crystal structure to a stress-induced martensitic (SIM) structure at certain temperatures, and return elastically to the austenitic structure when the stress is removed. These alternating crystalline structures provide the alloy with its super-elastic properties. One such well-known alloy, nitinol, is a nickel-titanium alloy. It is readily commercially available and undergoes the austenite-SIM-austenite transformation at a variety of temperature ranges between –20° C. and 30° C.

These alloys are especially suitable because of their capacity to elastically recover almost completely to the initial configuration once the stress is removed. Typically there is little plastic deformation, even at relatively high strains. This allows the guidewire to undertake substantial bends as it passes through the body's vasculature, and yet return to its original shape once the bend has been traversed without retaining any hint of a kink or a bend. However, the tips shown are often sufficiently plastic that the initial tip formation is retained. Nevertheless, compared to similar stainless steel guidewires, less force need be exerted against the interior walls of the vessels to deform the guidewire of the invention along the desired path through the blood vessel thereby decreasing trauma to the interior of the blood vessel and reducing friction against the coaxial catheter.

A guidewire, during its passage through the vasculature to its target site, may undertake numerous bends and loops. The desirably of enhancing the ease with which a guidewire may be twisted to allow the bent distal tip to enter a desired branch of the vasculature cannot be overstated. We have found that a major factor in enhancing such ease of use, that is, in enhancing the controllability of the guidewires is by controlling the eccentricity of the cross-section of the middle portion of the guidewire. We have found that by maintaining the middle portion of the guidewire (106 in FIG. 1) to an eccentricity ratio of $1\times10^{-4}$, the guidewire is significantly more controllable than those which fall outside this ratio. By "eccentricity", we mean that at any point along the guidewire the ratio of the largest diameter at that cross-section to the smallest diameter of the wire at that cross-section.

To achieve these results of high strength and enhanced control even while allowing feedback to the attending physician during use, we have found that the following physical parameters of the alloy are important. In a stress-strain test as shown on a stress-strain diagram such as that found in FIG. 8, the stress found at the midpoint of the upper plateau (UP) (measured, e.g. at about 3% strain when the test end point is about 6% strain) should be in the range of 75 ksi (thousand pounds per square inch)±10 ksi and, preferably, in the range of 75 ksi±5 ksi. Additionally, this material should exhibit a lower plateau (LP) of 25±7.5 ksi, preferably 20±2.5 ksi, measured at the midpoint of the lower plateau. The material preferably has no more than about 0.25% residual strain (RS) (when stressed to 6% strain and allowed to return) and preferably no more than about 0.15% residual strain.

The preferred material is nominally 50.6%±0.2% Ni and the remainder Ti. The alloy should contain no more than about 500 parts per million of any of O, C, or N. Typically such commercially available materials will be sequentially mixed, cast, formed, and separately co-worked to 30–40%, annealed and stretched.

Figure 8:
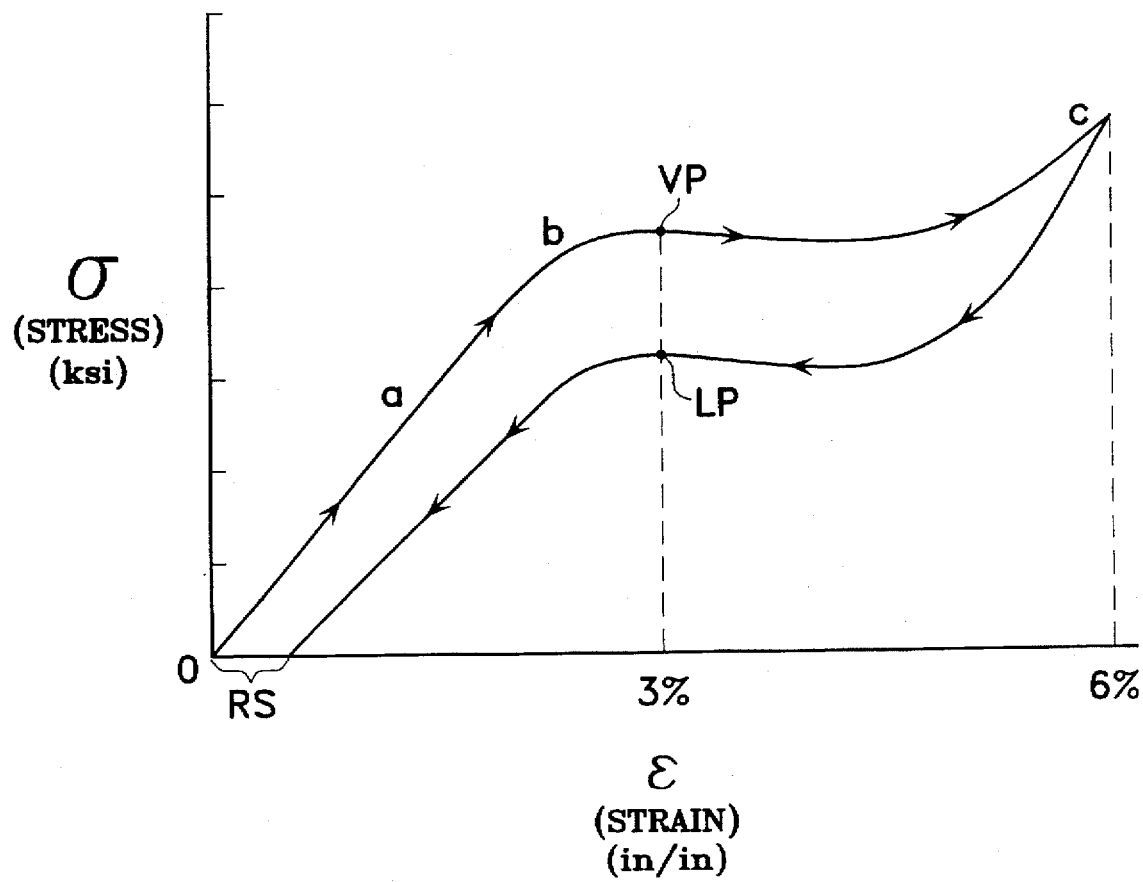
FIG. 8 shows a typical stress-strain diagram for a Ni—Ti alloy displaying objective criteria for selection of alloys for the inventive guidewire.

By way of further explanation, FIG. 8 shows a stylized stress-strain diagram showing the various parameters noted above and their measurement on that diagram. As stress is initially applied to a sample of the material, the strain is at first proportional (a) until the phase change from austentite to martensite begins at (b). At the upper plateau (UP), the energy introduced with the applied stress is stored during the formation of the quasi-stable martensite phase or stress-induced-martensite (SIM). Upon substantial completion of the phase change, the stress-strain relationship again approaches a proportional relationship at (c). The stress is no longer applied when the strain reaches 6%. The measured value (UP) is found at the midpoint between zero and 6% strain, i.e., at 3% strain. If another terminal condition of strain is chosen, e.g., 7%, the measured valued of (UP) and (LP) would be found at 3.5%.

Materials having high UP values produce guidewires which are quite strong and allow exceptional torque transmission but cause a compromise in the resulting "straightness" of the guidewire. We have found that guidewires having high UP values in conjunction with high LP values are not straight. These guidewires are difficult to use because of their tendency to "whip" as they are turned. Again, that is to say, as a guidewire is turned it stores energy during as a twist and releases it quickly. The difficulty of using such a whipping guidewire should be apparent. Materials having UP values as noted above are suitable as guidewires.

Furthermore, materials having values of LP which are high, again, are not straight. Lowering the value of LP compromises the ability of the guidewire to transmit torque but improves the ease with which a straight guidewire may be produced. Lowering the LP value too far, however, results in a guidewire which, although round, has poor tactile response. It feels somewhat "vague" and "soupy" during its use. The LP values provided for above allow excellent torque transmission, straightness, and the valuable tactile response.

The values of residual strain discussed above define a materials which do not kink or otherwise retain a "set" or configuration after stress during use as a guidewire.

EXAMPLE

In each instance, the following procedure was used in producing the data displayed in the table which follows: commercial Ni—Ti alloy wires having a nominal composition of 50.6% Ni and the remainder Ti, and diameters of 0.13", 0.16", or 0.18" were stressed at room temperature. In each instance, values for transition temperature, PS, UP, and LP were measured. Additionally, several of the noted wires were introduced into a U-shaped Tygon tube and spun to allow qualitative evaluation of the roundness and tactile response of the wires. Comments on that response are also found in the following table.

TABLE

| # | Comparative /Invention (C/I) | UP (ksi) | LP (ksi) | PS (%) | A* T °C. | Qualitative Spin Test |
|---|---|---|---|---|---|---|
| 1[1] | I | 74.48 | 31.45 | 0.06 | −11 | Smooth rotation, good feel |
| 2[2] | I | 76.94 | 18.90 | 0.121 | −8 | Smooth rotation, good feel |
| 3[3] | I | 71.92 | 24.06 | 0.10 | 13.5 | Smooth |
| 4[4] | C | 78.24 | 58.82 | 0.20 | −9 | Very rough turning, whipped |
| 5[5] | C | 63.80 | 13.25 | 0.2 | 12.5 | Smooth turning, mushy feel |
| 6[6] | C | 58.30 | 13.31 | 0.0 | −12 | Turned roughly, mushy feel |
| 7[7] | C | — | — | — | — | Difficult to turn |

[1]Commercially available from U.S. Nitinol Inc.
[2]Commercially available from Special Metals, Inc.
[3]Commercially available from Shape Metal Alloys, Inc.
[4]Commercially available as a plastic coated 0.13" guidewire from Fuji Terumo, Inc.
[5]Commercially available from ITI.
[6]Commercially available from Metal Tek
[7]Stainless Steel
*Measured at room temperature with no applied stress.

These data describe both guidewires made according to the invention and comparative guidewires. Additionally, they show that guidewire made from a typical stainless steel alloy is very difficult to turn using the qualitative test described above.

GUIDEWIRE CORE COATINGS

As mentioned above, all or part of the guidewire core may be covered or coated with one or more layers of a polymeric material. The coating is applied typically to enhance the lubricity of the guidewire core during its traversal of the catheter lumen or the vascular walls.

Coating Materials

As noted above, at least a portion of the guidewire core may simply be coated by dipping or spraying or by similar process with such materials as polysulfones, polyfluorocarbons (such as TEFLON), polyolefins such as polyethylene, polypropylene, polyesters (including polyamides such as the NYLON's), and polyurethanes; their blends and copolymers such as polyether block amides (e.g., PEBAX).

It is often desirable to utilize a coating such as discussed just above on the proximal portion of the guidewire and a coating such as discussed below on the more distal sections. Any mixture of coatings placed variously on the guidewire is acceptable as chosen for the task at hand.

The guidewire core may also be at least partially covered with other hydrophilic polymers including those made from monomers such as ethylene oxide and its higher homologs; 2-vinyl pyridine; N-vinylpyrrolidone; polyethylene glycol acrylates such as mono-alkoxy polyethylene glycol mono (meth) acrylates, including mono-methoxy triethylene glycol mono (meth) acrylate, mono-methoxy tetraethylene glycol mono (meth) acrylate, polyethylene glycol mono (meth) acrylate; other hydrophilic acrylates such as 2-hydroxyethylmethacrylate, glycerylmethacrylate; acrylic acid and its salts; acrylamide and acrylonitrile; acrylamidomethylpropane sulfonic acid and its salts cellulose, cellulose derivatives such as methyl cellulose ethyl cellulose, carboxymethyl cellulose, cyanoethyl cellulose, cellulose acetate, polysaccharides such as amylose, pectin, amylopectin, alginic acid, and cross-linked heparin; maleic anhydride; aldehydes. These monomers may be formed into homopolymers or block or random copolymers. The use of oligomers of these monomers in coating the guidewire for further polymerization is also an alternative. Preferred precursors include ethylene oxide; 2-vinyl pyridine; N-vinylpyrrolidone and acrylic acid and its salts; acrylamide and acrylonitrile polymerized (with or without substantial crosslinking) into homopolymers, or into random or block copolymers.

Additionally, hydrophobic monomers may be included in the coating polymeric material in an amount up to about 30% by weight of the resulting copolymer so long as the hydrophilic nature of the resulting copolymer is not substantially compromised. Suitable monomers include ethylene, propylene, styrene, styrene derivatives, alkylmethacrylates, vinylchloride, vinylidenechloride, methacrylonitrile, and vinyl acetate. Preferred are ethylene, propylene, styrene, and styrene derivatives.

The polymeric coating may be cross-linked using various techniques, e.g., by light such as ultraviolet light, heat, or ionizing radiation, or by peroxides or azo compounds such as acetyl peroxide, cumyl peroxide, propionyl peroxide, benzoyl peroxide, or the like. A polyfunctional monomer such as divinylbenzene, ethylene glycol dimethacrylate, trimethylolpropane, pentaerythritol di- (or tri- or tetra-) methacrylate, diethylene glycol, or polyethylene glycol dimethacrylate, and similar multifunctional monomers capable of linking the monomers and polymers discussed above.

Polymers or oligomers applied using the procedure described below are activated or functionalized with photoactive or radiation-active groups to permit reaction of the polymers or oligomers with the underlying polymeric surface. Suitable activation groups include benzophenone, thioxanthone, and the like; acetophenone and its derivatives specified as:

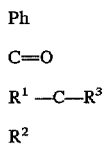

where $R^1$ is H, $R^2$ is OH, $R^3$ is Ph; or $R^1$ is H, $R^2$ is an alkoxy group including —$OCH_3$, —$OC_2H_3$, $R^3$ is Ph; or $R^1=R^2=$an alkoxy group, $R^3$ is Ph; or $R^1=R^2=$an alkoxy group, $R^3$ is H; or $R^1=R^2=$Cl, $R^3$ is H or Cl.

Other known activators are suitable.

The polymeric coating may then be linked with the substrate using known and appropriate techniques selected on the basis of the chosen activators, e.g., by ultraviolet light, heat, or ionizing radiation. Crosslinking with the listed polymers or oligomers may be accomplished by use of peroxides or azo compounds such as acetyl peroxide, cumyl peroxide, propionyl peroxide, benzoyl peroxide, or the like. A polyfunctional monomer such as divinylbenzene, ethylene glycol dimethacrylate, trimethylolpropane, pentaerythritol di- (or tri- or tetra-) methacrylate, diethylene glycol, or polyethylene glycol dimethacrylate, and similar multifunctional monomers capable of linking the polymers and oligomers discussed above is also appropriate for this invention.

The polymeric coating may be applied to the guidewire by any of a variety of methods, e.g., by spraying a solution or suspension of the polymers or of oligomers of the monomers onto the guidewire core or by dipping it into the solution or suspension. Initiators may be included in the solution or applied in a separate step. The guidewire may be sequentially or simultaneously dried to remove solvent after application of the polymer or oligomer to the guidewire and crosslinked.

The solution or suspension should be very dilute since only a very thin layer of polymer is to be applied. We have found that an amount of oligomer or polymer in a solvent of between 0.25% and 5.0% (wt), preferred is 0.5 to 2.0% (wt), is excellent for thin and complete coverage of the resulting polymer. Preferred solvents for this procedure when using the preferred polymers and procedure are water, low molecular weight alcohols, and ethers, especially methanol, propanol, isopropanol, ethanol, and their mixtures. Other water miscible solvents, e.g., tetrahydrofuran, methylene dichloride, methylethylketone, dimethylacetate, ethyl acetate, etc., are suitable for the listed polymers and must be chosen according to the characteristics of the polymer; they should be polar because of the hydrophilic nature of the polymers and oligomers but, because of the reactivity of the terminal groups of those materials, known quenching effects caused by oxygen, hydroxyl groups and the like must be recognized by the user of this process when choosing polymers and solvent systems.

Particularly preferred as a coating for the guidewire cores discussed herein are physical mixtures of homo-oligomers of at least one of polyethylene oxide; poly 2-vinyl pyridine; polyvinylpyrrolidone, polyacrylic acid, polyacrylamide, and polyacrylonitrile. The catheter bodies or substrates are preferably sprayed or dipped, dried, and irradiated to produce a polymerized and crosslinked polymeric skin of the noted oligomers.

The lubricious hydrophilic coating is preferably produced using generally simultaneous solvent removal and crosslinking operations. The coating is applied at a rate allowing "sheeting" of the solution, e.g., formation of a visibly smooth layer without "runs". In a dipping operation for use with most polymeric substrates including those noted below, the optimum coating rates are found at a linear removal rate between 0.25 and 2.0 inches/sec, preferably 0.5 and 1.0 inches/sec.

The solvent evaporation operations may be conducted using a heating chamber suitable for maintaining the surface at a temperature between 25° C. and the glass transition temperature ($T_g$) of the underlying substrate. Preferred temperatures are 50° C. to 125° C. Most preferred for the noted and preferred solvent systems is the range of 75° to 110° C.

Ultraviolet light sources may be used to crosslink the polymer precursors onto the substrate. Movement through an irradiation chamber having an ultraviolet light source at 90–375 nm (preferably 300–350 nm) having an irradiation density of 50–300 mW/cm$^2$ (preferably 150–250 mW/cm$^2$) for a period of three to seven seconds is desired. Passage of a guidewire core through the chamber at a rate of 0.25 to 2.0 inches/second (0.5 to 1.0 inches/second) in a chamber having three to nine inches length is suitable. When using ionizing radiation, a radiation density of 1 to 100 kRads/cm$^2$ (preferably 20 to 50 kRads/cm$^2$) may be applied to the solution or suspension on the polymeric substrate.

Exceptional durability of the resulting coating is produced by repetition of the dipping/solvent removal/irradiation steps up to five times. Preferred are two to four repetitions.

Tie Layers

We have found that it is often desirable to incorporate a "tie" layer as a coating between the outer polymeric surface and the guidewire core to enhance the overall adhesion of the outer-polymeric surface to the core. Of course, these materials must be able to tolerate the various other solvents, cleaners, sterilization procedures, etc. to which the guidewire and its components are placed during other production steps.

Figure 9:
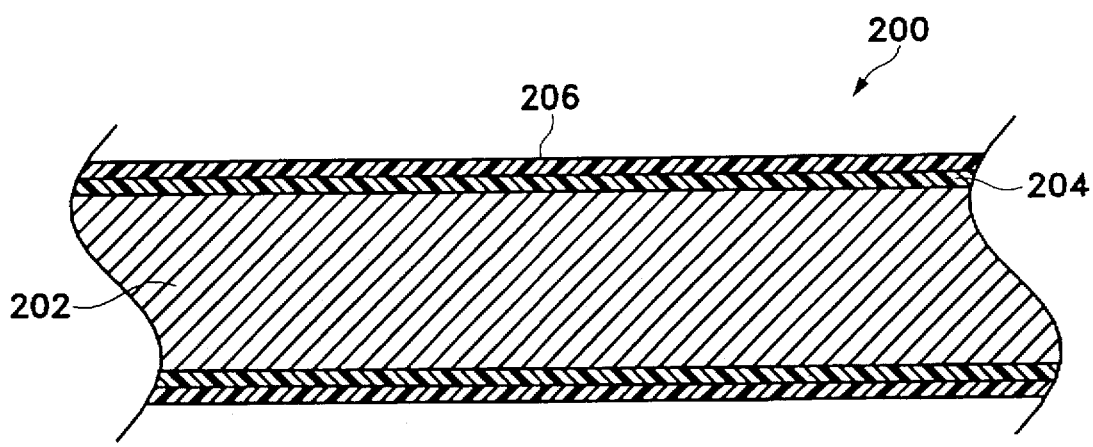
FIG. 9 is a partial cross-section of a guidewire section.

FIG. 9 shows a typical guide wire core section (200) having a metallic core (202), a polymeric tie layer (204), and a lubricious coating (206).

Choice of materials for such tie layers is determined through their functionality. Specifically, the materials are chosen for their affinity or tenacity to the outer polymeric lubricious or hydrophilic coating. Clearly, the tie layer material must be flexible and strong. The tie layers may be placed onto the guidewire core in a variety of ways. The polymeric material may be extrudable and made into shrinkable tubing for mounting onto the guidewire through heating. It may be placed onto the guidewire core by dipping, spraying, shrink wrapping of polymeric tubing or other procedure. One quite desireable procedure involves the placement of a polymeric tubing of a fusible polymer, e.g., polyurethane, on the guidewire core which, in turn, is covered with a heat shrink tubing such as polyethylene. The outer tubing is shrunk down and the inner tubing is fused onto the guidewire core to form a tie layer. The tie layer is preferably 0.0004" to 0.003" in thickness. The melt temperature of the tie layer polymer desireably is appropriatly chosen to fuse at the heat shrink temperature of the outer tubing. The outer shrink tubing is then simply peeled off, leaving the tie layer exposed for treatment with the lubricious coating.

We have found that various NYLON's, polyethylene, polystyrene, polyurethane, and polyethylene terephthalate (PET) make excellent tie layers. Preferred are polyurethane (Shore 80A–55D) and PET. Most preferred is polyurethane. It is additionally desireable to use a number of sections of polyurethane having differing hardnesses. For instance, the distal section may have a tie layer of Shore 80A polyurethane; the proximal shaft might be Shore D55 polyurethane. These materials may be formulated or blended to include radio opaque materials such as barium sulfate, bismuth trioxide, bismuth carbonate, tungsten, tantalum or the like.

As noted above, another manner of applying a tie layer is by heat-shrinking the tubing onto the guidewire. The guidewire core is simply inserted into a tubing of suitable size—often with a small amount of a "caulking" at either end to seal the tubing from incursion of fluids or unsterile materials from beneath the tubing. The tubing is cut to length and heated until it is sufficiently small in size. The resulting tubing tie layer desirably is between about 0.0005 and 0.015 inches in thickness. The thinner layers are typically produced from polyurethane or PET. The layer of lubricious polymer is then placed on the outer surface of the shrunk tubing.

Another procedure for preparing or pretreating guidewires prior to receiving a subsequent coating of a polymer, preferably a polymer which is lubricious, biocompatible, and hydrophilic, is via the use of a plasma stream to deposit a hydrocarbon or fluorocarbon residue. The procedure is described as follows: the guidewire core is placed in a plasma chamber and cleaned with an oxygen plasma etch. The guidewire core is then exposed to a hydrocarbon plasma to deposit a plasma-polymerized tie layer on the guidewire core to complete the pretreatment. The hydrocarbon plasma may comprise a lower molecular weight (or gaseous) alkanes such as methane, ethane, propane, isobutane, butane or the like; lower molecular weight alkenes such as ethene, propene, isobutene, butene or the like or; gaseous fluorocarbons such as tetrafluoromethane, trichlorofluoromethane, dichlorodifluoromethane, trifluorochloromethane, tetrafluoroethylene, trichlorofluoroethylene, dichlorodifluoroethylene, trifluorochloroethylene and other such materials. Mixtures of these materials are also acceptable. The tie layer apparently provides C—C bonds for subsequent covalent bonding to the outer hydrophilic polymer coating. Preferred flow rates for the hydrocarbon into the plasma chamber are in the range of 500 c.c./min. to 2000 c.c./min. and the residence time of the guidewire in the chamber is in the range of 1–20 minutes, depending on the chosen hydrocarbon and the plasma chamber operating parameters. Power settings for the plasma chamber are preferably in the range of 200 W to 1500 W.

A tie layer of plasma-produced hydrocarbon residue having a thickness on the order of 10 Å thick is disposed between core and coating. This process typically produces layers of hydrocarbon residue less than about 1000 Å in thickness, and more typically less than about 100 Å. Tie layer effectively bonds the outer layer to the guidewire core while adding very little additional bulk to the guidewire. Guidewires made according to this invention therefore avoid the size and maneuverability problems of prior art guidewires.

The pretreated guidewire may be coated by a polymer using a procedure such as described above. For example, the pretreated guidewire may be dipped in a solution of a photoactive hydrophilic polymer system, i.e., a latently photoreactive binder group covalently bonded to a hydrophilic polymer. After drying, the coated guidewire is cured by exposing it to UV light. The UV light activates the latently reactive group in the photoactive polymer system to form covalent bonds with crosslinked C—C bonds in the hydrocarbon residue tie layer. The dipping and curing steps are preferably repeated often enough, typically twice, to achieve the appropriate thickness of the hydrophilic coating layer.

One highly preferred variation of the invention involves a guidewire with metal core, preferably 0.010" to 0.025" diameter stainless steel or nitinol. The exterior surface of guidewire is a biocompatible coating of a polyacrylamide/polyvinylpyrrolidone mixture bonded to a photoactive binding agent. The preferred coating is made from a mixture of Bio-Metric Systems PA03 and PV05 (or PV01) binding systems according to the Examples below.

The photoactive hydrophilic polymer system of this preferred embodiment is a mixture of Bio-Metric Systems PA03 polyacrylamide/binder system and Bio-Metric Systems PV05 polyvinylpyrrolidone system. The polyacrylamide system provides lubricity, and the polyvinylpyrrolidone system provides both lubricity and binding for durability. The exact proportions of the two systems may be varied to suit the application. As an alternative, however, the hydrophilic biocompatible coating may be polyacrylamide alone, polyvinylpyrrolidone alone, polyethylene oxide, or any suitable coating known in the art. In addition, a coating of heparin, albumin or other proteins may deposited over the hydrophilic coating in a manner known in the art to provide additional biocompatibility features.

The guidewire or other device may be cleaned by using an argon plasma etch in place of the oxygen plasma etch. The thickness of the plasma-polymerized tie layer may also vary without departing from the scope of this invention.

The following examples are further illustrative of the articles and methods of this invention. The invention is not limited to these examples.

EXAMPLE

A 0.016" diameter nitinol guidewire was placed in a Plasma Etch MK II plasma chamber and cleaned with an oxygen plasma for 10 minutes. Methane flowing at a rate of 2000 c.c./min. was admitted into the chamber, and the chamber operated at a power setting of 400 W for 2 minutes to deposit a hydrocarbonaceous residue onto the surface of the wire. All but approximately six inches of the wire was dipped in a polyvinylpyrrolidone/polyacrylamide (PVP/PA) photocrosslinkable solution of a mixture of 67% BSI PV01 and 33% BSI PA03. The coated guidewire was then dried and exposed to an ultraviolet light (325 nm.) for 8 seconds. The dipping, drying, and exposing steps were repeated twice. When wetted, the resulting wire felt lubricious and required less force to pull through an 0.018" ID catheter than an uncoated wire.

EXAMPLE

A 0.016" diameter nitinol guidewire was placed in a Plasma Etch MK II plasma chamber and cleaned with an oxygen plasma for 10 minutes. Methane flowing at a rate of 1500 c.c./min. was admitted into the chamber, and the chamber was operated at a power setting of 600 W for 5 minutes to plasma-treat the methane into a hydrocarbonaceous residue on the surface of the wire. All but approximately six inches of the wire was dipped in a polyvinylpyrrolidone/polyacrylamide (PVP/PA) photocrosslinkable solution consisting essentially a mixture of 50% BSI PV01 and 50% BSI PA03. The coated guidewire was then dried and exposed to an ultraviolet light (325 nm.) for 8 seconds. The dipping, drying, and exposing steps were repeated. When wetted, the resulting wire felt lubricious and required less force to pull through an 0.018" ID catheter than an uncoated wire.

EXAMPLE

A 0.016" diameter nitinol guidewire was placed in a Plasma Etch MK II plasma chamber and cleaned with an oxygen plasma for 10 minutes. Ethane flowing at a rate of 900 c.c./min. was admitted into the chamber, and the chamber was operated at a power setting of 600 W for 10 minutes to deposit a hydrocarbon residue onto the surface of the wire. All but approximately six inches of the wire was dipped in a polyvinylpyrrolidone/polyacrylamide (PVP/PA) photocrosslinkable solution of a mixture of 33% BSI PV01 and 67% BSI PA03. The coated guidewire was then dried and exposed to an ultraviolet light (325 nm.) for 8 seconds. The dipping, drying, and exposing steps were repeated twice. When wetted, the resulting wire felt lubricious and required less force to pull through an 0.018" ID catheter than an uncoated wire.

EXAMPLE

A 0.013" diameter nitinol guidewire core was cleaned and introduced into a polyurethane tube (Shore 80A durometer hardness) having a 0.0015" wall thickness. The combination was then introduced into a heat-shrinkable polyethylene tubing. The dual layers of tubing were then heated to 350° to 400° F. whereupon the polyethylene tubing shrunk and the polyurethane tubing was fused to the wire core. The polyethylene tubing was then peeled off.

The polyurethane-metal core was then coated with eight layers of the Bio-Metric Systems PA03/PA05 material discussed above. The coated guidewire was then subjected to repetitive testing for loss of lubicity. The test involved introduction of the guidewire into a 0.028" ID catheter (150 cm length) situated in a water bath, the distal end of the catheter being connected to a glass labyrinth analogizing to a vascular network.

Figure 10:
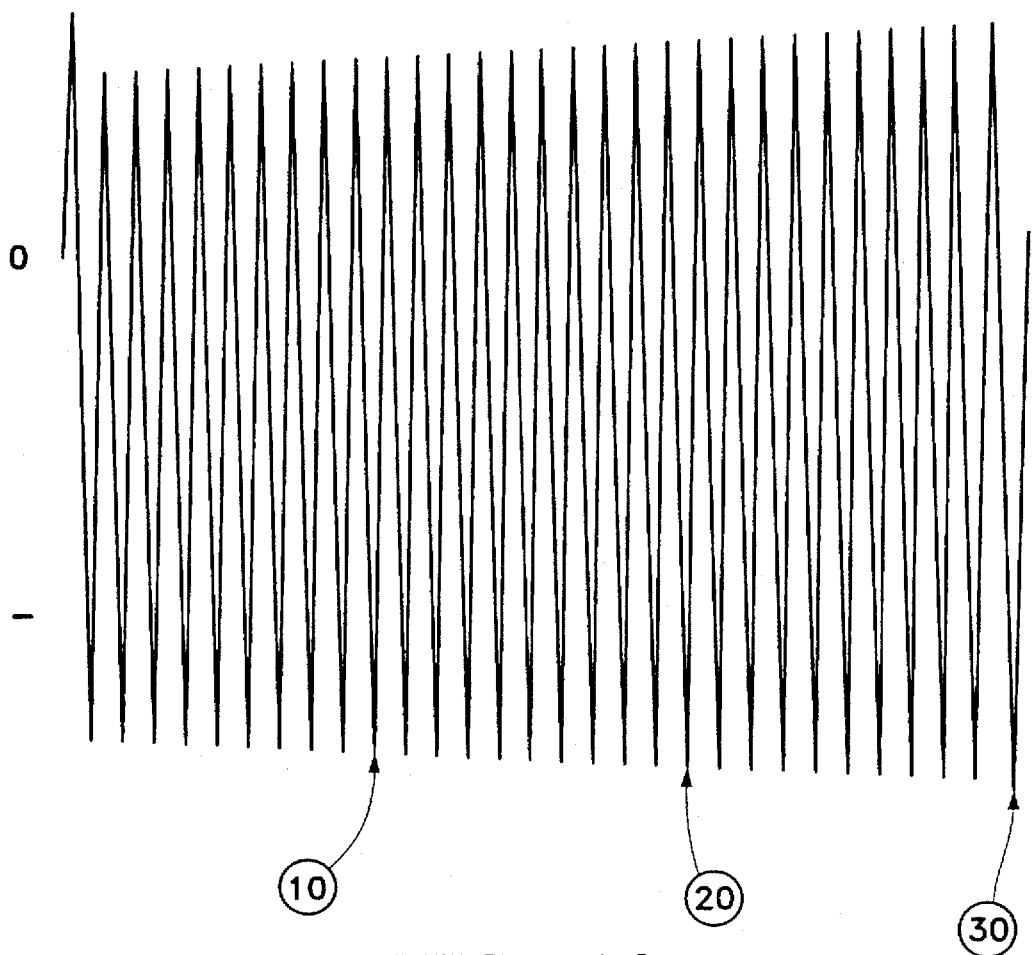
FIG. 10 is a graph showing friction on a guidewire test, the guidewire being made according to the invention.

The guidewire was then stroked over a 1" distance for a specified number of times—in this case, 30 strokes—and the friction measured. The measured friction on this catheter is shown in FIG. 10. The absolute value of the friction is not shown; the fact that the friction did not increase is to be noticed in FIG. 10. This demonstrates that the outer lubricious layer did not degrade during the test.

Although preferred embodiments of the present invention have been described, it should be understood that various changes, adaptations, and modifications may be made therein without departing from the spirit of the invention and the scope of the claims which follow.

We claim as our invention:

1. A guidewire section suitable for guiding a catheter within a blood vessel, comprising
   a.) an elongated flexible metal wire core having a proximal section and a distal tip section.
   b.) a polymeric tie layer disposed about at least a portion of said distal section,
   c.) a lubricious polymer layer disposed about the polymeric tie layer, and
   d.) a malleable metal wire coil disposed about another distally located portion of said distal tip section, said malleable metal wire coil having a section length uncoated by said polymeric tie layer.

2. The guidewire section of claim 1 where the metal core is a super-elastic Ni—Ti alloy material.

3. The guidewire section of claim 1 where the metal core is nitinol.

4. The guidewire section of claim 1 where the metal core is stainless steel.

5. The guidewire section of claim 1 where the tie layer comprises at least one of NYLON, polyethylene, polystyrene, polyurethane, and polyethylene terephthalate.

6. The guidewire section of claim 5 where the tie layer comprises polyethylene terephthalate or polyurethane.

7. The guidewire section of claim 1 where the tie layer is polyurethane.

8. The guidewire section of claim 1 where the tie layer comprises a fused polyurethane.

9. The guidewire section of claim 1 where the tie layer is polyurethane and has a variable hardness distally.

10. The guidewire section of claim 1 where the tie layer further comprises one or more radio opaque materials selected from barium sulfate, bismuth trioxide, bismuth carbonate, tungsten, and tantalum.

11. The guidewire section of claim 1 additionally comprising a layer disposed about the tie layer comprising polymers produced from monomers selected from ethylene oxide; 2-vinyl pyridine; N-vinyl-pyrrolidone; polyethylene glycol acrylates such as monoalkoxy polyethylene glycol mono(meth) acrylates, including mono-methoxy triethylene glycol mono (meth) acrylate, mono-methoxy tetraethylene glycol mono (meth) acrylate, polyethylene glycol mono (meth) acrylate; other hydrophilic acrylates such as 2-hydroxyethylmethacrylate, glycerylmethacrylate; acrylic acid and its salts; acrylamide and acrylonitrile; acrylamidomethylpropane sulfonic acid and its salts, cellulose, cellulose derivatives such as methyl cellulose ethyl cellulose, carboxymethyl cellulose, cyanoethyl cellulose, cellulose acetate, polysaccharides such as amylose, pectin, amylopectin, alginic acid, and cross-linked heparin.

12. A guidewire section suitable for guiding a catheter within a body lumen, comprising
    a) an elongated, flexible metal wire core of a super-elastic alloy having a UP of 75 ksi±10 ksi, an LP of 25±7.5 ksi measured at 3% strain and a PS of less than 0.25% where measured in a stress-strain test to 6% strain, and
    b) a polymeric tie layer coaxially located about the wire area.

13. The guidewire section of claim 12 in which the super-elastic alloy is Ni—Ti.

14. The guidewire section of claim 12 in which the super-elastic alloy is nitinol.

15. The guidewire section of claim 12 where the tie layer is comprised of at least one of NYLON, polyethylene, polystyrene, polyurethane, and polyethylene terephthalate.

16. The guidewire section of claim 12 where the tie layer is comprised of polyurethane or polyethylene terephthalate.

17. The guidewire section of claim 12 where the tie layer is polyurethane.

18. The guidewire section of claim 12 where the tie layer is polyurethane fused to the core.

19. The guidewire section of claim 12 wherein the tie layer is polyurethane and has a variable hardness distally.

20. The guidewire section of claim 12 in which at least a portion of the polymeric tie layer is coated with a lubricious polymeric material.

21. The guidewire section of claim 16 where the lubricious polymeric material comprises polymers produced from monomers selected from ethylene oxide; 2-vinyl pyridine; N-vinylpyrrolidone; polyethylene glycol acrylates such as mono-alkoxy polyethylene glycol mono(meth) acrylates, including mono-methoxy triethylene glycol mono (meth) acrylate, mono-methoxy tetraethylene glycol mono (meth) acrylate, polyethylene glycol mono (meth) acrylate; other hydrophilic acrylates such as 2-hydroxyethylmethacrylate, glycerylmethacrylate; acrylic acid and its salts; acrylamide and acrylonitrile; acrylamidomethylpropane sulfonic acid and its salts, cellulose, cellulose derivatives such as methyl cellulose ethyl cellulose, carboxymethyl cellulose, cyanoethyl cellulose, cellulose acetate, polysaccharides such as amylose, pectin, amylopectin, alginic acid, and cross-linked heparin.

22. The guidewire section of claim 21 where the lubricious polymeric material comprises a mixture of polyvinyl pyrrolidone and polyacrylamide.

23. The guidewire section of claim 12 where the tie layer additionally comprises a radio isopaque material selected from barium sulfate, bismuth trioxide, bismuth carborate, tungsten, and tantalum.

24. The guidewire of claim 12 additionally comprising a catheter sheath.

* * * * *

UNITED STATES PATENT AND TRADEMARK OFFICE
CERTIFICATE OF CORRECTION

PATENT NO. : 5,749,837

DATED : May 12, 1998

INVENTOR(S) : Palermo et al.

It is certified that error appears in the above-identified patent and that said Letters Patent is hereby corrected as shown below:

*Column 3, line 33*: please change "11 to 1 kg/mm$^2$" to -- 11 to 12 kg/mm$^2$ --.

*Column 3, line 61*: please change "75+10 ksi" to -- 75±10 ksi --.

*Column 3, line 62*: please change "25+7.5 ksi" to -- 25±7.5 ksi --.

*Column 8, line 46*: please change "1×10$^{-4}$" to -- 1±10$^{-4}$ --.

Signed and Sealed this

Twenty-fifth Day of August, 1998

Attest:

BRUCE LEHMAN

*Attesting Officer*      *Commissioner of Patents and Trademarks*